United States Patent
Hammer et al.

(10) Patent No.: US 7,756,569 B2
(45) Date of Patent: Jul. 13, 2010

(54) METHOD FOR MEASURING THE VESSEL DIAMETER OF OPTICALLY ACCESSIBLE BLOOD VESSELS

(75) Inventors: Martin Hammer, Jena (DE); Walthard Vilser, Rudolstadt (DE)

(73) Assignee: IMEDOS GmbH, Jena (DE)

( * ) Notice: Subject to any disclaimer, the term of this patent is extended or adjusted under 35 U.S.C. 154(b) by 834 days.

(21) Appl. No.: 11/547,059

(22) PCT Filed: Mar. 31, 2005

(86) PCT No.: PCT/DE2005/000587

§ 371 (c)(1),
(2), (4) Date: Oct. 2, 2006

(87) PCT Pub. No.: WO2005/094668

PCT Pub. Date: Oct. 13, 2005

(65) Prior Publication Data

US 2007/0276260 A1 Nov. 29, 2007

(30) Foreign Application Priority Data

Apr. 2, 2004 (DE) .................. 10 2004 017 130

(51) Int. Cl.
*A61B 6/00* (2006.01)
*A61B 5/02* (2006.01)
*G01C 1/06* (2006.01)
*G01J 1/42* (2006.01)
*G01B 11/00* (2006.01)
*G01B 11/02* (2006.01)

(52) U.S. Cl. .................. 600/476; 600/500; 356/139; 356/223; 356/388; 356/635

(58) Field of Classification Search .................. None
See application file for complete search history.

(56) References Cited

U.S. PATENT DOCUMENTS

| 6,535,757 | B2 * | 3/2003 | Ono ........................... 600/476 |
| 6,690,816 | B2 * | 2/2004 | Aylward et al. ............. 382/128 |
| 6,798,515 | B1 * | 9/2004 | Bachelder et al. ........... 356/397 |
| 2004/0064057 | A1 | 4/2004 | Siegel |
| 2005/0107710 | A1 * | 5/2005 | Nakayama .................. 600/500 |

FOREIGN PATENT DOCUMENTS

| DE | 196 48 935 | 5/1998 |
| EP | 0 397 377 | 11/1990 |
| WO | 00/65986 | 11/2000 |

\* cited by examiner

*Primary Examiner*—Long V Le
*Assistant Examiner*—Angela M Hoffa
(74) *Attorney, Agent, or Firm*—Frommer Lawrence & Haug LLP

(57) ABSTRACT

It is the object of a method for measuring the vessel diameter of optically accessible blood vessels to measure vessel diameters of optically accessible blood vessels in a simple manner based on digital images and with high accuracy even when the vessel diameter is on an order of magnitude at which the determination of the diameter by image point counting is associated with an unacceptably high error. According to the invention, the vessel diameter is determined photometrically from the logarithmized ratio of the intensities of the reflection of the vessel-free environment of the blood vessel and of the reflection of the blood vessel, which intensities are determined in a first monochromatic image.

14 Claims, 1 Drawing Sheet

METHOD FOR MEASURING THE VESSEL DIAMETER OF OPTICALLY ACCESSIBLE BLOOD VESSELS

CROSS-REFERENCE TO RELATED APPLICATIONS

This application claims priority of International Application No. PCT/DE2005/000587, filed Mar. 31, 2005 and German Application No. 10 2004 017 130.0, filed Apr. 2, 2004, the complete disclosures of which are hereby incorporated by reference.

BACKGROUND OF THE INVENTION a) Field of the Invention

The invention is directed to a method for determining the diameter of optically accessible blood vessels based on digital images showing the blood vessels and their environment. The method according to the invention is provided in particular for application to the fundus of the human eye but is not limited thereto.

b) Description of the Related Art

The vessel diameter of blood vessels and changes in the vessel diameter due to provocation or stimulation of the metabolism are an important physiological measurement quantity.

Known methods for determining the vessel diameter in optically accessible vessels, for example, in those of the oculus fundus, are often planimetric methods which are implemented in a manner suitable for the evaluation of digitally recorded images or digitized images in image processing programs.

A method of this kind is known, for example, from DE 196 48 935 A1, which determines the vessel diameter based on vessel edge acquisition as the distance between photometric vessel edge centroids formed by interpolation with corrected oblique position of the vessel edges. This method achieves a reproducibility that enables significant individual detection of regulatory changes.

However, a disadvantage arises from the geometric measurement of the vessel diameter based on digital images because the measuring accuracy is limited by the resolution of the raster of digital image points. When the vessel diameters reach an order of magnitude in the range of a few image points, this increases the error in the geometric measurement.

OBJECT AND SUMMARY OF THE INVENTION

Therefore, it is the primary object of the invention to measure vessel diameters of optically accessible blood vessels in a simple manner based on digital images and with high accuracy even when the vessel diameter is on an order of magnitude at which the determination of the diameter by means of image point counting is associated with an unacceptably high error.

According to the invention, the above-stated object is met in a method of the type described above for determining the vessel diameter of optically accessible blood vessels in that the vessel diameter is determined photometrically from the logarithmized ratio of the intensities of the reflection of the vessel-free environment of the blood vessel and of the reflection of the blood vessel, which intensities are determined in a first monochromatic image.

In order to eliminate different oxygen saturations, the first monochromatic image is preferably based on an isosbestic wavelength of the hemoglobin.

Vignetting, which almost inevitably occurs in the optical image, can be corrected in that the intensities of the reflections determined in the first monochromatic image are scaled to intensities of the reflections obtained from a second monochromatic image of another wavelength which is recorded simultaneous with the first monochromatic image.

In a particularly advantageous manner, the blood vessels and their environment are illuminated for simultaneous recording of the spectrally different monochromatic images simultaneously with different wavelengths of an illumination beam which correspond to the spectral difference of the images to be recorded, each wavelength being adapted to a color channel of a color camera serving to record the images so that it is received by this color channel.

Detection of the blood vessels, their direction and their vessel-free environment can be carried out automatically by image-processing means or manually. In this way, specular reflections on the blood vessels can be identified and eliminated.

When measuring the reflection values perpendicular to the direction of the blood vessel, an average is taken over the reflection values of all of the image points associated with the blood vessel. A plurality of reflection values which are averaged perpendicular to the direction of the blood vessel can be determined along the direction of the blood vessel and the average is taken over these averaged reflection values.

In a special development of the invention, the determination of the vessel diameter is carried out as a reaction to physiological provocation or stimulation. This can be carried out in different ways, e.g., by flicker light, by inhalation of oxygen or carbogen by the test subject.

A method which is particularly suitable for optical influence consists in that light from at least one light source is modified through programming techniques by a light manipulator arranged in an illumination beam path of an image-generating device, and the modified light is used for illumination and for selective provocation or stimulation.

The vessel diameter of the blood vessels which is determined by the method according to the invention can be used in a variety of ways for diagnostic purposes. Advantageous applications in this connection are indicated in the dependent claims.

The invention will be described more fully in the following with reference to the schematic drawings.

DESCRIPTION OF THE PREFERRED EMBODIMENTS

Figure 1:
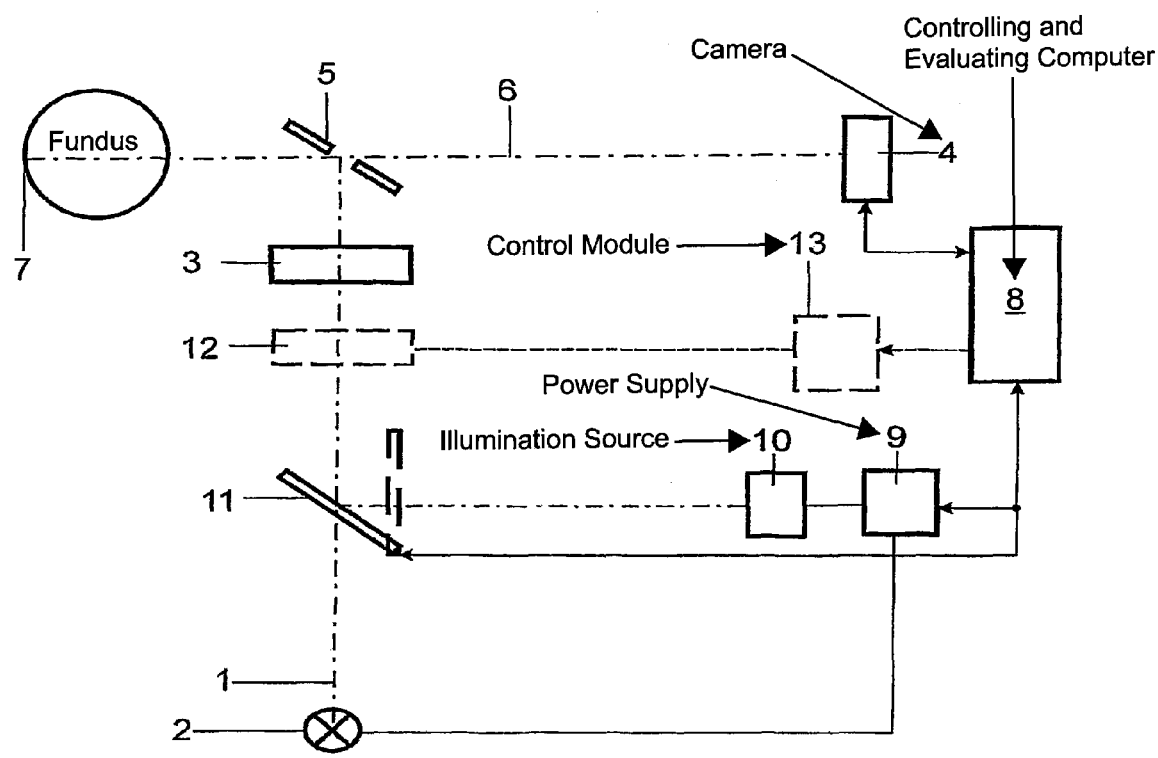
FIG. 1 shows a simplified view of the construction of an image-generating device for implementing the method according to the invention.

The image-generating device shown in a simplified view in FIG. 1 can be used to implement the method according to the invention which can be applied preferably, but not exclusively, to blood vessels of the ocular fundus.

In principle, the method according to the invention can be applied to optically accessible (and identifiable) blood vessels of biological objects of which the monochromatic congruent images, preferably in different spectra, which are required for the photometric determination of the vessel diameter of the blood vessels can be recorded, for example, also with a slit lamp, an endoscope or a surgical microscope.

According to the present embodiment example, the images of the fundus of the eye are recorded at an isosbestic wavelength $\lambda_i=548$ mm of the hemoglobin and, if required for correction of the vignetting that inevitably occurs in every optical image, additionally at a different wavelength $\lambda_n$.

This may be carried out, for example, with a simple retina camera, shown in FIG. 1, that has been modified in an extremely economical manner, whose illumination system contains in a common illumination beam path 1 at least one illumination source 2 and, particularly for implementing the method according to the invention, a filter device 3 which prepares wavelengths on the illumination side which are spectrally tuned to the color channels of an electronic color camera 4. Further, one of the components known from retina camera technology is a perforated mirror 5. A recording beam path 6 passes through the central opening of this perforated mirror 5. The illumination light is directed through optically imaging elements, not shown here, to the fundus 7 and particularly to the blood vessels located therein and their environment over an area surrounding the central opening. Light reflected by the fundus 7 passes along the recording beam path 6 and along optically imaging elements, not shown, to an image-generating recording system. In the present embodiment example, the color camera 4 is provided for this purpose. The camera control of the color camera 4 is connected to a central controlling and evaluating unit, particularly a controlling and evaluating computer 8. A power supply 9 serving to supply power to the two illumination sources 2 and 10 is also connected to the controlling and evaluating computer 8 and likewise corresponding tilting mirror controls.

Of course, implementation of the method according to the invention is not limited to this construction of a retina camera. Depending on the medical inquiry, many different modifications can be carried out, or other image-generating devices can be used. For example, it is possible to provide only the continuous illumination source 2 or only the illumination source 10 which is constructed as a strobe illumination source, or to use both of them together as is shown in FIG. 1. The means for coupling the latter into the common illumination beam path 1, which is carried out conventionally in this instance by a swing-out mirror 11, can also be carried out in different ways.

Figure 2:
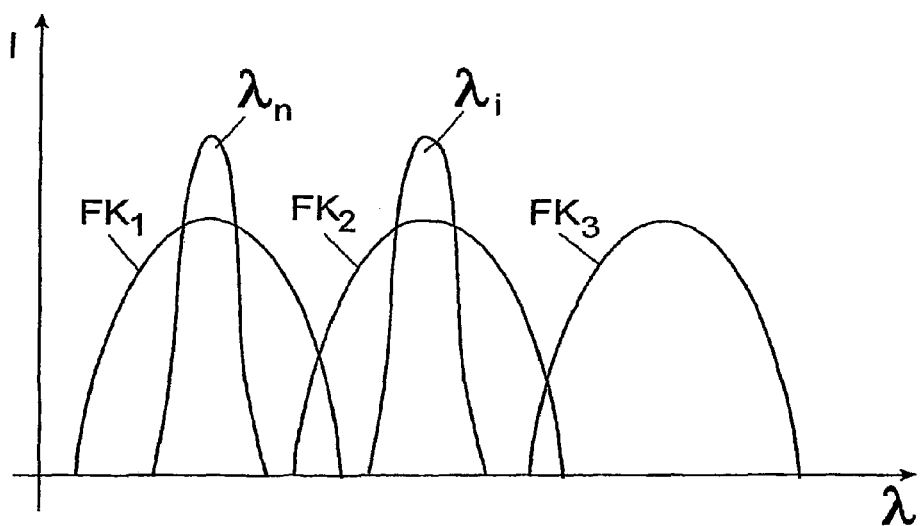
FIG. 2 shows the position of selected wavelength ranges in the color channels when the wavelength ranges prepared on the illumination side are adapted to the color channels with respect to color matching.

However, when two spectrally different monochromatic images are to be generated simultaneously in an advantageous manner with the method according to the invention at the isosbestic wavelength, the filter device 3 must be selected based on the spectral characteristic of the color camera 4 and inserted in the illumination beam path 1 in order to illuminate the fundus 7 simultaneously and with different colors at different wavelengths $\lambda_i$ and $\lambda_n$, each of these wavelengths being tuned to one of the color channels $FK_j$ (j=1, 2, 3) of the color camera 4 with respect to a color matching corresponding to FIG. 2.

Suitable optical filters 3 are layer filters such as dual bandpass filters or triple bandpass filters which are suitable particularly for subsequent integration in the illumination beam path 1 of already existing systems, preferably in a parallel beam portion. A geometrically structured filter comprising sector-shaped filter regions with different spectral filter characteristics whose sectors can have identical or different sector surface contents is also suitable but must be arranged in the vicinity of the aperture plane.

The intensities of the reflections in the image of the blood vessels and their vessel-free environment which are to be identified automatically preferably by means of an image-processing algorithm at $\lambda_i=548$ nm are determined, and the vessel diameter is determined based on these intensities in a manner which will be described in the following.

The image points neighboring the blood vessels are used as environment when no other vessel is detected therein. After the vessel direction is determined, an average is preferably formed perpendicular to this direction from the reflection values of all of the image points associated with the blood vessel. In so doing, specular reflections on the blood vessel can be excluded from the averaging. It is also possible to determine in vessel direction a plurality of reflection values which are averaged perpendicular to the vessel direction and to use these in turn to form a (sliding) average. Averaging can also be carried out in the vessel environment in a similar manner.

The image of a biological structure with embedded vessel is formed as the result of a very complex process of the light propagation in the tissue involving dispersion, reflection and absorption, both within the vessel and in or on the vessel walls and in the surrounding tissue. Surprisingly, however, it was possible to establish a relationship between vessel diameter and the intensity of the reflection diameter for small blood vessels with vessel diameters from about 20 µm to 80 µm and limited to 100 µm in that the logarithmized ratio of the intensities of the reflection of the vessel-free environment of the blood vessel ($R_u$) and the reflections of the blood vessel ($R_g$) is proportional to the vessel diameter d:

$$d = a \cdot \log \frac{R_u}{R_g} \qquad (1)$$

For calibration of the image used for determining diameter, the proportionality factor a can be found either from a model of the beam transport in the blood vessel, in the vessel wall and in the surrounding biological tissue or through a comparison with a sufficiently thick vessel from the same image that was measured by a conventional geometric measurement method. The proportionality factor a is preferably determined by comparing with a reference vessel whose vessel diameter is sufficiently large (upward of approximately 100 µm) that it can be determined by the method according to DE 196 48 935 A1. The image-specific proportionality factor a from (1) is given by the diameter value obtained in this way in connection with the measured reflections of the vessel-free environment of the blood vessel and of the blood vessel itself.

The method according to the invention makes it possible to show the vessel structure in the image of the biological object in which the vessel diameter is coded, for example, in false colors. A static evaluation of the vessel diameters of all vessels in the image and of the ratios of the vessel diameters of the arteries to the vessel diameters of the veins when compared with normal values allows a general diagnosis of existing pathologies.

Additional important diagnostic information is provided by the reaction of the vessel diameter to physiological provocation or stimulation (e.g., by illumination of the eye with flicker light, inhalation of oxygen or carbogen by the patient). By comparing the measurements before, during and after physiological provocation or stimulation, the reaction of individual vessel portions with respect to the change in vessel diameter can be observed. Vessel portions exhibiting a pathological reaction to provocation or stimulation can be determined by comparison with findings elicited in the same way from healthy test subjects and can be identified in the image.

For this purpose, the image-generating device according to FIG. 1 can have additional means which are also suitable for stimulation or provocation of the blood vessels such as a controllable optical light manipulator 12 which is arranged in the common illumination beam path 1 next to the filter device 3 and whose control module 13 has an interface to the controlling and evaluating computer 8 (shown in dashes).

The light manipulator 12 which is controllable in a variety of ways by programming is shared between all of the illumination sources and, by modifying primary light, in this case the continuously emitting illumination source 2 and the strobe illumination source 10, generates secondary light.

The light manipulator is suitable for programmable modification of the light of at least one light source with respect to its intensity curve and/or time curve in a temporally defined relationship with the adjustments of the at least one light source, the image recording and the evaluation for adaptively accommodating to the examination task. The secondary light can be used for illumination and for selective provocation or stimulation. Therefore, multifunctionality can be achieved by influencing the illumination by means of an individual element arranged in the illumination beam path in that the light characteristics of the light guided in the illumination beam path are changed so as to be adapted to function.

By recording and evaluating pulse-synchronized sequences of images, systolic and diastolic differences in vessel diameter can be obtained as diagnostic features. Combining the measured vessel diameters with other local or general characteristic values of microcirculation such as oxygen saturation in the blood vessels being examined, the blood flow rate or blood pressure enables a detailed description of the oxygen supply and metabolism in the tissue.

While the foregoing description and drawings represent the present invention, it will be obvious to those skilled in the art that various changes may be made therein without departing from the true spirit and scope of the present invention.

The invention claimed is:

1. A method for determining the vessel diameter of optically accessible blood vessels based on digital, monochromatic images showing intensities of reflections of the blood vessels and a vessel-free environment, the vessel-free environment being an environment surrounding the blood vessels, comprising:
    illuminating the blood vessels and the vessel-free environment with a light source for simultaneous recording of spectrally different monochromatic images simultaneously with different wavelengths of an illumination beam, which correspond to a spectral difference of the image, each wavelength adapted to a color channel of a color camera serving to record the images received by the color channel;
    detecting blood vessels, a longitudinal direction of the blood vessels, and the vessel-free environment from the images;
    determining the intensities of reflections of the blood vessels and the vessel-free environment;
    scaling the intensities of the reflections determined in a first monochromatic image to intensities of reflections obtained from a second monochromatic image of a different wavelength which is recorded simultaneously with the first monochromatic image; and
    determining the vessel diameter, within a range of 20 to 100 micrometers, from a logarithmized ratio of an intensity of a reflection of the vessel-free environment of the blood vessel and the intensity of a reflection of the blood vessel, the intensities being determined in the first monochromatic image.

2. The method according to claim 1;
wherein the first monochromatic image is based on an isosbestic wavelength of hemoglobin.

3. The method according to claim 1;
wherein an average is taken perpendicular to the longitudinal direction of the blood vessel over reflection values of all of the image points associated with the blood vessel.

4. The method according to claim 3;
wherein a plurality of reflection intensities, which are averaged perpendicular to the longitudinal direction of the blood vessel, is determined along the longitudinal direction of the blood vessel, and an average is taken over the averaged reflection intensities.

5. The method according to claim 4;
wherein specular reflections on the blood vessels are identified and eliminated by image-processing means.

6. The method according to claim 1;
wherein the determination of the vessel diameter is carried out as a reaction to physiological provocation or stimulation.

7. The method according to claim 6;
wherein the physiological provocation or stimulation is produced by flicker light.

8. The method according to claim 7;
wherein light from at least one light source is modified through programming techniques by a light manipulator arranged in an illumination beam path of an image-generating device; and
wherein the modified light is used for illumination and for selective provocation or stimulation.

9. The method according to claim 7;
wherein the physiological provocation or stimulation is produced by inhalation of oxygen by a test subject.

10. The method according to claim 7;
wherein the physiological provocation or stimulation is produced by inhalation of carbogen by a test subject.

11. The method according to claim 1;
wherein a representation of the spatial arrangement of the blood vessels is produced in which the vessel diameter is coded.

12. The method according to claim 1;
wherein a diagnostic criterion is formed by means of a statistical evaluation of the determined vessel diameters of blood vessels and of ratios calculated among vessel diameters from selected vessels.

13. The method according to claim 1;
wherein systolic and diastolic differences in vessel diameter are obtained as diagnostic features by recording pulse-synchronized sequences of images.

14. The method according to claim 1;
wherein the determined vessel diameters are used in combination with other local or general characteristic values of microcirculation to determine oxygen supply and metabolism in a tissue region.

* * * * *